United States Patent [19]

Pope

[11] Patent Number: 5,895,757

[45] Date of Patent: Apr. 20, 1999

[54] ENCAPSULATION OF LIVING TISSUE CELLS IN INORGANIC MICROSPHERES PREPARED FROM AN ORGANOSILICON

[76] Inventor: Edward J. A. Pope, 447 Lorenzo Dr., Agoura, Calif. 91301

[21] Appl. No.: 08/912,771

[22] Filed: Aug. 18, 1997

Related U.S. Application Data

[63] Continuation-in-part of application No. 08/371,064, Jan. 10, 1995, Pat. No. 5,739,020, application No. 08/627,212, Nov. 8, 1995, Pat. No. 5,693,513, and application No. 08/560,380, Nov. 17, 1995, Pat. No. 5,757,124, which is a division of application No. 08/084,876, Jun. 30, 1993, Pat. No. 5,480,582, said application No. 08/627,212, is a continuation-in-part of application No. 08/371,064.

[51] Int. Cl.[6] ............... C12N 11/14; C12N 11/04; C12N 5/00

[52] U.S. Cl. ............... 435/176; 435/182; 435/382; 435/420

[58] Field of Search ............... 435/174, 176, 435/395, 420

[56] References Cited

U.S. PATENT DOCUMENTS

| | | | |
|---|---|---|---|
| 4,148,689 | 4/1979 | Hino et al. | 435/182 |
| 4,391,909 | 7/1983 | Lim | 435/178 |
| 4,797,213 | 1/1989 | Parisims et al. | 210/651 |
| 5,200,334 | 4/1993 | Dunn et al. | 435/182 |
| 5,693,513 | 12/1997 | Pope | 435/176 |
| 5,739,020 | 4/1998 | Pope | 435/176 |
| 5,744,337 | 4/1998 | Price et al. | 435/178 |

*Primary Examiner*—David M. Naff
*Attorney, Agent, or Firm*—W. Edward Johansen

[57] ABSTRACT

Living tissue cells such as from an animal or a plant are encapsulated in inorganic microspheres. An organosilicon precursor such as tetraethoxysilane or an organometallic precursor such as aluminum tri-n-propoxide is hydrolyzed in an aqueous acidic solution to form a gel forming solution. Tissue cells are mixed with a salt solution such as Hanks' Balanced Salt Solution to form a solution containing the tissue cells. The solution containing tissue cells and the gel forming solution are mixed to form a mixture. The mixture is mixed with an oil that is immiscible with the mixture and has a lower specific density than the mixture. The resultant mixture is stirred to form microspheres encapsulating the tissue cells. The mixture containing the tissue cells and the gel forming solution may be formed into droplets and added to the top of a column containing the oil to form the microspheres.

2 Claims, 1 Drawing Sheet

ENCAPSULATION OF LIVING TISSUE CELLS IN INORGANIC MICROSPHERES PREPARED FROM AN ORGANOSILICON

This application is a continuation-in-part of application Ser. No. 08/371,064, filed Jan. 10, 1995, now U.S. Pat. No. 5,739,020; and is a continuation-in-part of application Ser. No. 08/627,212, filed Nov. 8, 1995, now U.S. Pat. No. 5,693,513, which is a continuation-in-part of the application Ser. No. 08/371,064; and is a continuation-in-part of application Ser. No. 08/560,380, filed Nov. 17, 1995, now U.S. Pat. No. 5,757,124, which is a division of application Ser. No. 08/084,876, filed Jun. 30, 1993, now U.S. Pat. No. 5,480,582.

BACKGROUND OF THE INVENTION

The field of the invention is an encapsulation of living tissue cells in a microsphere.

The following patents and textual material are hereby incorporated by reference into the specification.

A process for synthesizing amorphous silica microspheres includes the steps of placing into a container an organosilicon precursor and a highly acidic solution and stirring the organosilicon precursor and the highly acidic solution at a stirring rate sufficient to form droplets of the organosilicon precursor in the highly acidic solution. Water in the highly acidic solution hydrolizes the droplets of the organosilicon precursor to form amorphous silica microspheres. The stirring rate is in the range between 8 Hz to 50 Hz. The highly acidic solution has a solar concentration in the range of 0.05 to 2.5. The organo-silicon precursor and the highly acidic solution are immiscible. The volumetric ratio of the organosilicon precursor to the highly acidic solution is in the range from 8 to 1 to 18 to 1. The organosilicon precursor is selected from a group consisting of tetraethoxysilane (TEOS), tetrabutoxysilane (TBOS), tetramethoxysilane (TMOS) and tetrapropoxysilane (TPOS). The highly acidic solution is selected from a group consisting of nitric acid ($HNO_3$) and hydrochloric acid (HCl).

U.S. Pat. No. 4,983,369 teaches a process for producing highly uniform microspheres of silica having an average diameter of 0.1–10 microns from the hydrolysis of a silica precursor. The process is characterized by employing precursor solutions and feed rates which initially yield a two-phase reaction mixture.

U.S. Pat. No. 4,943,425 teaches a method of making high purity, dense silica of large particles size. Tetraethylorthosilicate is mixed with ethanol and is added to a dilute acid solution having a pH of about 2.25. The resulting solution is digested for about 5 hours, then 2N ammonium hydroxide is added to form a gel at a pH of 8.5. The gel is screened through an 18–20 mesh screen, vacuum baked, calcined in an oxygen atmosphere and finally heated to about 1200 C. in air to form a large particle size, high purity, dense silica.

U.S. Pat. No. 4,251,387 teaches techniques for producing semipermeable microcapsules by interfacial polymerization. The material to be encapsulated and a hydrophilic monomer are emulsified within a hydrophobic continuous phase. Polymerization is initiated by dissolving a second monomer in the continuous phase, and occurs only at the interface of the emulsion to result in the formation of macroporous, poorly defined capsule membranes. Next, the affinity of the continuous phase for the hydrophilic monomer is varied by altering the polarity of the continuous phases This step is accomplished either by isolating and resuspending the raw phase of different polar character, or by mixing a second solvent with the continuous phase. By controlling the affinity and the concentration of the second monomer, it is possible to produce microcapsules having uniform capsule membranes and a selected upper limit of permeability.

U.S. Pat. No. 4,246,349 teaches bacteria which are immobilized by adsorption on an inorganic carrier. The bacteria are stabilized by carrying out the adsorption procedure in the presence of frog about 1 to about 20% weight per volume of sucrose of nonfat dry milk solids and lyophilizing the adsorbed bacteria.

U.S. Pat. No. 4,391,909 teaches tissue cells which are encapsulated within a spheroidal semipermeable membrane including a polysaccharide having acidic groups cross-linked with a polymer having a molecular weight greater than 3,000. The tissue cells may be islet of Langerhans cells or liver cells. The tissue cells within the microcapsules are viable, healthy, physiologically active and capable of ongoing metabolism. The encapsulated cells are useful for implantation in a mammalian body to produce substances and effect chemical changes which are characteristic of the cells in vivo tissue.

U.S. Pat. No. 5,371,018 teaches a process for qualitative or quantitative determination of a reactive liquid sample which includes the steps of forming doped sol-gel glass pellets from a metal alkoxide, arranging the porous doped sol-gel glass pellets in a glass tube, contacting a liquid sample containing a reactive chemical with the porous doped sol-gel glass pellets contained in the glass tube and measuring a length of a stained portion of the glass tube resulting from a color change in the sol-gel glass pellets. The sol-gel glass pellets are formed by a gelling step conducted at room temperature in the presence of a colorimetric reagent dopant which produces a color change in the presence of the reactive chemical and a drying step which is conducted at not greater than 41 C. The doped sol-gel glass pellets contain the colorimetric reagent dopant which is encapsulated therein. The encapsulated colorimetric reagent using doped sol-gel glasses dopant is color changeable in the presence of the reactive chemical in the pores of the doped sol-gel glass pellets.

U.S. Pat. No. 4,148,689 teaches the immobilization of microorganisms which is carried out by mixing a water soluble-polymer selected from polyvinyl-alcohol, gelatin and carboxymethylcellulose with a tetraalkoxysilane, hydrolyzing the resulting mixture by the addition of acid to form a homogeneous complex sol, dispersing microbial cells homogeneously in the sol and gelling the mixture of the sol and microbial cells.

U.S. Pat. No. 5,453,368 teaches a method for encapsulating a biological substance which includes the steps of maintaining a coating-forming liquid film sheet comprising a solution of a soluble organic polymer in an organic solvent, causing droplets consisting of a biological substance in an aqueous medium to pass through the sheet to form microcapsules which includes cores of the droplets coated by the liquid film and permitting the microcapsules to pass through the sheet so that a portion of the polymer precipitates in the presence of water in the droplets while evaporating a portion of the solvent to form a continuous permeable polymer coating of sufficient structural that the microcapsules are self-supporting.

U.S. Pat. No. 5,395,808 teaches inorganic supports which are porous bodies. The inorganic supports are suitable for use as supports for microorganism. The bodies have a significantly large average pore diameter of about 0.5 to 100 microns and a total pore volume of about 0.1 to 1.5 cc/g with the large pores contributing a pore volume of from about 0.1 to 1.0 cc/g. The porous bodies are made by preparing a mixture of ultimate particles of bound clay, one or more optional ingredients such as inorganic binders, extrusion or forming aids, burnout agents, or a forming liquid, such as water. The microorganism may be selected from a group consisting of fungi, yeast, protozoans and algae. The microorganism may also be bacteria selected from the group consisting of Pseudomonas, Acinetobacter, Vibrio, Mycobacterium, Actinomycetes, Corynebacterium, Bacillus, Arthrobacterium, Flavobacterium, Beijerinckia, Achromobacterium, Alcaligenes, Azotobacter, Xanthomonas, Nitrobacter, Nitrosomonas, Methylosinus, Methylococcus, Nocardia and Methylobacter. Many other types of bacteria are contemplated as being able to exist in the large pores.

U.S. Pat. No. 4,246,349 teaches bacteria which is immobilized by adsorption on an inorganic carrier which are stabilized by carrying out the adsorption procedure in the presence of from about 1 to about 20% weight per volume of sucrose of nonfat dry milk solids and lyophilizing the adsorbed bacteria.

The sol-gel process is a versatile techniqiue for making silica ceramics with porosity ranging from a few percent to as high as 99 percent. Sol-gel processes proceed under mild conditions so that a variety of delicate materials may be incorporated into the inorganic gel. The sol-gel process for incorporating cells into an inorganic gel involves three basic steps of staining the cells to follow their geometric distribution with the gel, forming the gel forming solution and monitoring cell metabolisms Saccharomyces cerevesiae cells (brewer's yeast) are an ideal model organism for gel-encapsulated microorganisms. The yeast cells are stained with 8-hydroxy-1, 3,6 trisulfonated pyrene trisodium salt (pyranine dye). The pyranine dye are used as molecular probes for water content, pH changes in phospholipid vesicles and the chemical processes in aluminoslicate sols and gels. Pronated pyranine, which exists at low-pH, shows a strong blue luminescence when excited by radiation at 430 nanometers while the depronated pyranine, which exists at high-pH, fluoresces at 515 nanometers when excited by radiation at 365 nanometers. Alcohol/water ratios can be followed by measuring the relative luminescence/fluorsecence at the two wavelengths.

Another process for synthesizing a sol-gel encapsulating an active biological material includes the steps of placing into a container an organosilicon precursor from a group consisting of tetramethoxysilane (TEOS), tetrabutoxysilane (TBOS), tetratethoxysilane (TMOS) and tetrapropoxysilane (TPOS), and a highly acidic solution from a group consisting of nitric acid ($HNO_3$) and hydrochloric acid (HCl) having a molar concentration of acid in the range of 0.05 to 2.5 and stirring the organosilicon precursor and the highly acidic solution. The water in the highly acidic solution hydrolizes the organosilicon precursor. The process also includes the steps of adding a base solution having a molar concentration of base in the range of 0.05 to 2.5 from a group consisting of ammonium hydroxide and stirring the organosilicon precursor, the highly acidic solution and the base solution. The process further includes the steps of adding a prestained Saccharomyces cerevesiae dispersion and stirring the organosilicon precursor, the highly acidic solution, the base solution and the prestained Saccharomyces cerevesiae dispersion to make a gel forming solution. The gel forming solution is cast into a test tube to form an inorganic gel.

In an experiment tetraethoxysilane (TEOS) and hydrochloric acid (HCl) having a molar concentration of 0.1 were placed into a container to form a turbid mixture. After one half hour the turbid mixture becomes clear because of hydrolysis of the tetraethoxysilane and the evolution of ethanol. Ammonium hydroxide having a molar concentration of 0.1 is added to neutralize the clear mixture and then a stained yeast dispersion is introduced into the neutralized clear mixture. After the yeast cells are mixed in, portions of the sol-gel are poured into polyethylene tubes and stored at 5 C. Gels appear beige under normal illumination and fluroresce bright green at 365 nanometers. The average pore size for the matrix is 10 nanometers and the average size of the yeast cells is about 10 microns. The yeast cells are essentially "shrink-wrapped" inside the silicon-oxygen-silicon matrix. Pore size is sufficient for nutrients to reach the cells on all sides, but the pores are much smaller than the yeast cells themselves. The size difference between pore size and cell size—a factor of 1000—illustrate the gentleness of the sol-gel process. The yeast cells are not lysed and continue to function after the matrix closes in around them.

U.S. Pat. No. 4,138,292 teaches an enzyme or microorganism which is entrapped within the gel matrix of a sulfated polysaccharide in the presence of ammonium ion, a metal ion, a water-soluble amine or a water-miscible organic solvent.

U.S. Pat. No. 5,149,543 teaches a synthetic polymeric capsule which encapsulates a biologically-labile materials such as proteins, liposomes, bacteria and eucaryotic cells. The method is based on the use of a water-soluble polymer with charged side chains that are crosslinked with multivalent ions of the opposite charge to form a gel encapsulating biological material, that is optionally further stabilized by interactions with multivalent polyions of the same charge as those used to form the gel.

U.S. Pat. No. 5,227,298 teaches a method of encapsulating viable tissue cells within a double walled bead and a method of pretreating the tissue cells with an immunosuppressant.

U.S. Pat. No. 5,294,446 teaches osteoprogenitor cells which are encapsulated in alginate and alternatively, additionally encapsulated in poly-L-lysine and/or agarose promote regeneration of bone at the site of implantation. A composition includes osteoprogenitor cells which are either embedded or encapsulated in alginate. The use of the microcapsules facilitates bone regeneration.

Braun described in "Biochemically Active Sol-Gel Glasses: The Trapping Of Enzymes," Materials Letters, Vol. 10, No. 1, Sep. 2, 1990, pp. 1–5, the encapsulation of an enzyme in a sol-gel glass. Braun reported that the activities of the encapsulated enzyme was only about 30%.

U.S. Pat. No. 5,200,334 teaches the forming of a single phase sol by mixing a metal alkoxide in a non-alcoholic medium which includes an acid catalyst. The active biological material is selected from the group consisting of nuclease, protease, oxidase, esterase, isomerase, metal and metal ion binders, bicarbonate binders, free radical inhibitors, reversible oxygen binders and combinations thereof. The active biological material is selected from the group consisting of RNase A, RNase T1, protease k, chymotrypsin, alcohol oxidase, glucose oxidase, acetylcholine esterase, phosphodiesterase II, aldolase, glucose isomerase, hemoglobin, myoglobin, cytochrome c, aequorin, transferase, urease, superoxide dismutase and combinations thereof. The active biological material is a protein.

U.S. Pat. No. 5,200,334 also teaches an active biological material in a glass which is formed using a sol-gel process.

A metal alkoxide is mixed with water and exposed to ultrasonic energy at a ph=<2 to form a single phase solution which is buffered to a pH between about 5 and 7. The buffered solution is then mixed with the active biological material and the resultant gel is aged and dried. The dried products is a transparent porous glass with substantially all of the added active biological material encapsualted therein the biological material retaining a high level of activity. Suitable acid catalysts include mineral acids such as hydrochloric acid, sulfuric acid, nitric acid, phosphoric acid, etc. and organic acids such as acetic acid, tartaric acid, phthalic acid, maleic acid, succinic acid and the like and anhydrides of the mineral or organiconium, niobium, hafnium, chromium, vanadium, tungsten, molybdenum, iron, tin, phosphorus, sodium, calcium, and boron, or combinations thereof. Suitable biological materials for encapsulation include, but are not limited to, nucleases, such as RNase A or RNase T1, proteases, such as proteinase K or chymotrypsin, oxidases, such as alcohol oxidase or glucose oxidase, esterases, such as acetylcholine esterase or phosphodiesterase II, isomerases, such as aldolase or glucose isomerase, various proteins including O.sub.2 binders, such as hemoglobin or myoglobin, electron transfer proteins, such as cytochrome c, metal and metal ion binders, such as aequorin, iron and bicarbonate binders, such as transferrin, free radical inhibitors, such as superoxide dismutase and other active biologicals such as ureases. One skilled in the art can readily supplement this list with other biological materials which can be entrapped in an inorganic gel. The entrapped material is not a limiting factor. Additionally, the biological materials may be modified or tagged by addition of readily detected substituents such as ions, ligands, optically active groups or other constituents commonly used to tag biological or chemical compounds. Suitable luminescent tags include Mn.sup.2+ and other rare earth metal ions.

The process includes the steps of initiating the acid catalyzed hydrolysis of a metal alkoxide in water without added alcohol by applying ultrasonic energy. Silicon compounds are preferred because silicon chemistry is highly conducive to forming glasses. Among silicon compounds, tetraethoxysilane is preferred over other materials, such as tetraethoxysilane, because it reacts faster and does not require alcohol to form a sol. The precursor material or the gel forming solution may be tagged by known methods with readily detected substituents, such as optically active groups or constituents which respond to the byproducts of the action of the proteins. Alternatively, other optically active materials may be encapsulated with the protein as indicators of the results of reactions involving the proteins. Other optically active materials include luminescent amino acids, such as tryptophan, or other similar materials.

U.S. Pat. No. 5,292,801 teaches a process for the preparation of a reactive sol-gel glass, comprising polymerizing at least one monomer of the formula $M(R)_n (P)_m$ and elected from the group consisting of metal alkoxides, semi-metal alkoxides, metal esters and semi-metal esters, wherein M is a metallic or semi-metallic element, R is a hydrolyzable substituent, n is an integer of 1 to 6, P is a non-polymerizable substituent and m is an integer of 0 to 6, and optionally an organic monomer, under acidic, neutral or basic conditions and in the presence of a dopant to form a porous xerogel containing the dopant trapped therein. M is at least one metal selected from the group consisting of Si, Al, Ti and Pb. R is at least one substituent selected from the group consisting of alkyl, aryl, alkoxy and aryloxy groups, and n is 2, 3 or 4. The polymerization includes a gelling step conducted at not greater than room temperature and a drying step conducted at not greater than 45 C. The dopant is selected from the group consisting of organic compounds, stable organic radicals, organometallic compounds, inorganic compounds and molecules of biological origin. The dopant is reactive after preparation of the xerogel.

U.S. Pat. No. 5,292,801 teaches a method which obtains a chemical interaction between at least one reagent trapped in a glass, which is formed by a sol gel process, by doping it with a reagent and diffusable solutes or components in an adjacent liquid or gas phase. The reagents, the solutes or the components can be any organic or inorganic compounds or materials of biologically orgin including enzymes. The doped sol-gel glass in various forms may be useful as an analytical test, chromatographic medium, sensor, catalyst or biocatalyst, electrode or enzyme electrode or other detection device.

U.S. Pat. No. 4,438,198 teaches a biochemically active matrix for use in a bio-artificial organ which has an enzyme covalently bonded to a matrix of organochemically cross-linked fibrin. The matrix may be suspended in a medium of agarose which irreversibly solidifies below 37 C. The bio-artificial organ is useful for extracorporeal treatment of blood to remove excess substrate from the blood.

U.S. Pat. No. 5,290,692 teaches a fibrin-inolytic enzyme such as urikinase, tissue plasminogen activator or streptokinase which is covalently bounded to a bioadaptable porous crystalline glass to produce a thrombolytic material. Production of the glass involves combining 40–50 mol % calcium oxide, 20–30 mol % titanium dioxide and 25–35 mol % diphosphorous pentoxide to form a mixture, and combining the mixture with 0.5–4.0 mol % disodium oxide. A bioreactor for converting plasminogen in blood into plasmin can be prepared by packing the material in a column. When finely comminuted, the material can be administered into the blood of a patient for removing blood clots.

U.S. Pat. No. 5,171,579 teaches a composition which includes a pharmaceutically acceptable admixture of an osteogenic protein, a porous particulate polymer matrix and an osteogenic protein-sequestering amount of blood clot.

U.S. Pat. No. 5,364,839 teaches osteoinductive pharmaceutical formulations which include antifibrinolytic agents such as epsilon amino acid caproic acid or other lysine analogues or serine protease inhibitors and cartilage and/or bone inductive proteins are disclosed. These formulations are useful in the treatment of cartilage and/or bone defects.

SUMMARY OF INVENTION

The present invention is generally directed to a process for encapsulating a living tissue cell in a microsphere. The process for encapsulating living tissue cells in a plurality of microspheres includes the steps of mixing an organometallic precursor and a hydrolyzing solution to form a gel forming solution, mixing living tissue cells and a salt solution to form a solution containing living tissue cells and mixing the solution containing living tissue cells with the gel forming solution to form a mixture of a specific density.

In a first separate aspect of the present invention, the process also includes the steps of mixing the mixture into a container containing an oil and stirring the mixture to form a plurality of microspheres each of which encapsulates some of the living tissue cells. The oil is immiscible with the mixture and has a lower specific density than the specific density of the mixture.

In a second separate aspect of the present invention, the process also includes the steps of forming droplets of the mixture and putting the droplets into a column of an oil. The oil is immiscible with the mixture and has a lower specific density than the specific density of the mixture at the top thereof to form a plurality of microspheres each of which encapsulates some of the living tissue cells.

In a third separate aspect of the present invention, the organosilicon precursor is selected from a group consisting of tetraethoxysilane, tetrabutoxysilane, tetramethoxysilane and tetrapropoxysilane.

In a fourth separate aspect of the present invention, the living tissue cells are from an animal.

In a fifth separate aspect of the present invention, the living tissue cells are from a plant.

Other aspects and many of the attendant advantages will be more readily appreciated as the same becomes better understood by reference to the following detailed description.

The features of the present invention which are believed to be novel are set forth with particularity in the appended claims.

DESCRIPTION OF THE PREFERRED EMBODIMENT

Figure 1:
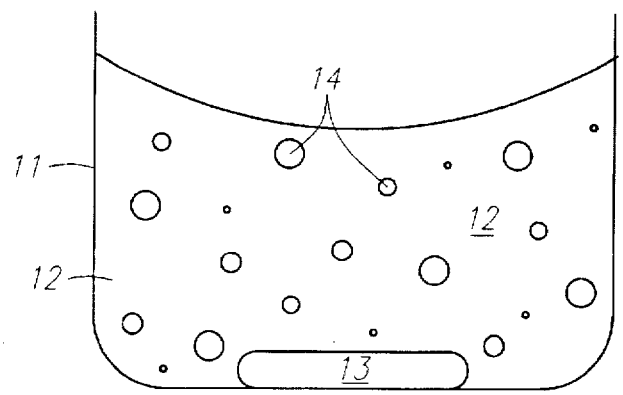
FIG. 1 is a side elevation of a stir bar and a container which contains an oil and into which the mixture of the solution containing living tissue cells with the gel forming solution to form a mixture according to the first embodiment of the present invention.

A process for synthesizing a sol-gel encapsulating living tissue cells includes the steps of placing into a first container an organometallic precursor and a hydrolyzing solution, stirring the solution until the solution becomes clear, chilling the clear solution in an ice bath, placing into a second container living tissue cells and a balanced salt solution to form a tissue solution.

Living tissue cells are harvested. The living tissue cells are placed in a balanced salt solution to form a tissue solution. The living tissue cells may be from either a plant or an animal. U.S. Pat. No. 4,797,213 teaches the use of Hanks' balanced salt solution in Column 6, line 10.

The organometallic precursor may be an organosilicon precursor and the hydrolyzing solution may be a highly acidic solution having a molar concentration of acid in the range of 0.05 to 2.5. The process also includes the steps of adding a base solution having a molar concentration of base in the range of 0.05 to 2.5 to the clear solution, immediately thereafter adding the tissue solution to the clear solution and the base solution, stirring the clear solution, the base solution and the tissue solution to form a gel forming solution and casting the gel forming solution into a test tube to form an inorganic gel encapsulating the tissue cells of an animal.

The organosilicon precursor may be selected from a group consisting of tetraethoxysilane, tetrabutoxysilane, tetramethoxysilane, tetrapropoxysilane and methyl trimethyloxysilane. The organometallic precursor may be selected from a group consisting of aluminum tri-n-propoxide, aluminum tri(sec)butoxide, aluminum acetoacetic ester chelate di(sec)butoxide, zirconium tri(sec)butoxide, boron butoxide, boron methoxide, titanium (iv) butoxide, titanium isopropoxide and zirconium isopropoxide. The highly acidic solution is selected from a group consisting of nitric acid ($HNO_3$) and hydrochloric acid (HCl). Other highly acidic solutions may also be used including sulfuric acid ($H_2SO_4$). In the preferred embodiment the base solution is ammonium hydroxide. Please refer to C. J. Brinker, *Journal of Non-Crystaline Solutions*, Volume 48, page 48 and Volume 63, page 45.

Chapter 13 on page 141 of the book entitled *Animal Cell Culture*, edited by Jeffrey W. Pollard and John M. Walker and published by Humana Press which is located in Clifton, N.J., describes Hanks' Balanced Salt Solution.

The manual entitled *Plant Tissue Culture Manual: Fundamentals and Applications*, edited by K. Lindsey and published by Humana Press. Tissue cells of a plant may be harvested from a leaf by grinding the leaf into leaf-fragments. The leaf-fragments are placed in a balanced salt solution to form a plant tissue solution.

Chapter 13 on page 141 of the book entitled *Animal Cell Culture*, edited by Jeffrey W. Pollard and John M. Walker and published by Humana Press which is located in Clifton, N.J., also describes the harvesting of tissue cells of an animal.

Tissue cells of an animal may be harvested from the liver, the pancreas, the thyroid, the parathyroid, the pituitary gland and the renal cortex of mammels including man. The sol-gel which encapsulates one of these tissue cells may be used in an artificial organ such as either an artificial liver or an artificial pancreas.

For example, living animal tissue cells have been harvested from beef liver (bovine hepatocytes). The standard procedure for dispersing living animal tissue cells is to cut beef liver into small cubes. About 10 grams of the small cubes of beef liver are placed in 60 milliliters of Hanks' balanced salt solution for one half hour in order to remove the hemoglobin from the beef lever. The Hanks' balanced salt solution is removed. Forty milligrams of collagenase and sixty milligrams of dispase are dissolved in the Hanks' balanced salt solution. Dispase and collagenase are enzymes. The Hanks' balanced salt solution is shaken for one half hour and decanted to form a tissue solution. The tissue solution is a supernatent solution which has individual living liver cells dispersed therein. The inventor has encapsulated liver cells in an organic gel.

U.S. Pat. No. 5,270,192 teaches a hepatocyte bioreactor, a bioartificial liver, which includes a containment vessel having a perfusion inlet and a perfusion outlet, a matrix within the containment vessel so as to entrap hepatocyte aggregates within the containment vessel while allowing perfusion of the matrix.

U.S. Pat. No. 4,391,909 teaches tissue cells such as islet of Langerhans cells or liver cells which are encapsulated within a spheroidal semipermeable membrane including a polysaccharide having acidic groups cross-linked with a polymer having a molecular weight greater than 3,000. The cells within the microcapsules are viable, healthy, physiologically active and capable of ongoing metabolism. The encapsulated cells are useful for implantation in a mammalian body to produce substances and effect chemical changes characteristic of the cells in vivo tissue. The inventor has encapsulated islet of Langerhans cells in an organic gel.

U.S. Pat. No. 5,166,058 teaches purified BMP-2 proteins which may be used in the treatment of bone and cartilage defects and in wound healing and related tissue repair. For bone and/or cartilage formation, the composition includes a matrix capable of delivering BMP-2A, BMP-2B or other BMP protein to the site of bone and/or cartilage damage, providing a structure for the developing bone and cartilage and optimally capable of being resorbed into the body. Such matrices may be formed of materials presently in use for other implanted medical DNA sequences encoding the osteoinductive proteins applications. The choice of matrix material is based on biocompatibility, biodegradability, mechanical properties, cosmetic appearance and interface properties. The particular application of the BMP-2 compositions will define the appropriate formulation. Potential matrices for the compositions may be biodegradable and chemically defined calcium sulfate, tricalciumphosphate, hydroxyapatite, polylactic acid and polyanhydrides. Other potential materials are biodegradable and biologically well defined, such as bone or dermal collagen. Further matrices consists of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalciumphosphate. The bioceramics may be altered in composition, such as in calcium-aluminate-phosphate and processing to alter pore size, particle size, particle shape, and biodegradability. The dosage regimen will be determined by the attending physician considering various factors which modify the action of the BMP-2 protein, e.g. amount of bone weight desired to be formed, the site of bone damage, the condition of the damaged bone, the size of a wound, type of damaged tissue, the patient's age, sex, and diet, the severity of any infection, time of administration and other clinical factors. The dosage may vary with the type of matrix used in the reconstitution and the types of BMP proteins in the composition. The addition of other known growth factors, such as IGF I (insulin like growth factor I), to the final composition, may also effect the dosage.

The biological substance of U.S. Pat. No. 5,453,368 includes PC-12 cells which were cultured in standard RPMI. The cells were taken up by pipette, placed in centrifuge tubes and spun down. The cells were brought up to a volume of 2 ml, to a cell concentration of approximately $2 \times 10^6$ to $5 \times 10^6$ per ml. The cell containing liquid was placed in sterile Hamilton syringe and placed on a Harvard apparatus injector pump. The pump was connected via 18 gauge polytetrafluoroethylene tubing to a 24 gauge stainless steel tube, which served as an apparatus for dropping the liquid. Microcapsules containing bovine adrenal chromaffin cells in a 1.5% sodium alginate solution (W/V) were prepared. The PBS collection bath container contained 1.5% (W/V) calcium chloride. After six weeks in culture, the microcapsules contained viable cells.

Referring to FIG. 1 a process for encapsulating a living tissue cell in a microsphere. The process for encapsulating living tissue cells in a plurality of microspheres includes the steps of mixing an organometallic precursor and a hydrolyzing solution to form a gel forming solution, mixing living tissue cells and a salt solution to form a solution containing living tissue cells and mixing the solution containing living tissue cells with the gel forming solution to form a mixture of a specific density. The living tissue cells are from either an animal or a plant. The process also includes the steps of mixing the mixture into a container 11 containing an oil 12 and stirring with a stir bar 13 the mixture to form a plurality of microspheres 14. Each microsphere 14 encapsulates some of the living tissue cells. The oil 12 is immiscible with the mixture and has a lower specific density than the specific density of the mixture. The organometallic precursor may be a organosilicon precursor. The organosilicon precursor may be selected from a group consisting of tetraethoxysilane, tetra-butoxysilane, tetramethoxysilane and tetra-propoxysilane.

Figure 2:
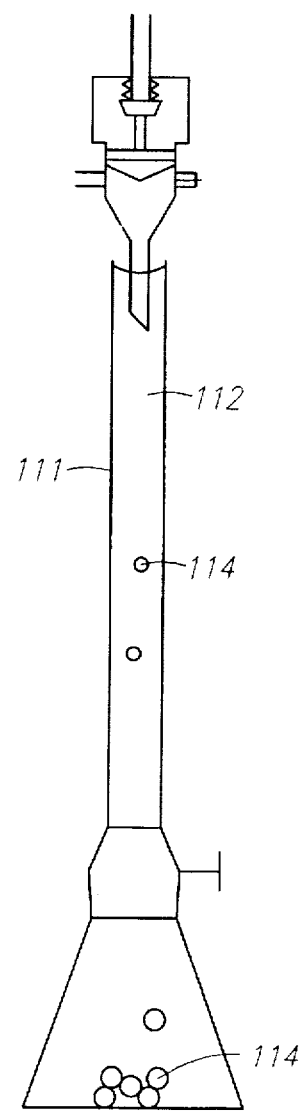
FIG. 2 is a side elevation of a dropper and a column of an oil into which the mixture of the solution containing living tissue cells with the gel forming solution to form a mixture according to the second embodiment of the present invention.

Referring to FIG. 2 a process for encapsulating a living tissue cell in a microsphere. The process for encapsulating living tissue cells in a plurality of microspheres includes the steps of mixing an organometallic precursor and a hydrolyzing solution to form a gel forming solution, mixing living tissue cells and a salt solution to form a solution containing living tissue cells and mixing the solution containing living tissue cells with the gel forming solution to form a mixture of a specific density. The living tissue cells are from either an animal or a plant. The process also includes the steps of forming droplets of the mixture and putting the droplets into a column 111 of an oil 112. The oil 112 is immiscible with the mixture and has a lower specific density than the specific density of the mixture at the top thereof to form a plurality of microspheres. Each microsphere 114 encapsulates some of the living tissue cells. The organometallic precursor may be a organosilicon precursor. The organosilicon precursor may be selected from a group consisting of tetraethoxysilane, tetra-butoxysilane, tetramethoxysilane and tetra-propoxysilane.

From the foregoing it can be seen that a sol-gel encapsulating an active biological materials, including tissue cells of an animal and micro-organisms, has been described. Accordingly it is intended that the foregoing disclosure shall be considered only as an illustration of the principle of the present invention.

What is claimed is:

1. A process for encapsulating living tissue cells in a plurality of inorganic microspheres comprising the steps of:
   a. mixing an organosilicon precursor and a hydrolyzing solution which is a highly aqueous acidic solution having a molar concentration of acid in the range of 0.05 to 2.5 to form a gel forming solution wherein said organosilicon precursor is selected from a group consisting of tetraethoxysilane, tetrabutoxysilane, tetramethoxysilane and tetrapropoxysilane;
   b. mixing living tissue cells and Hanks' Balanced Salt Solution to form a solution containing living tissue cells;
   c. mixing the solution containing living tissue cells resulting from step b with the gel forming solution resulting from step a to form a mixture of a specific density;
   d. mixing the mixture resulting from step c into a container containing an oil which is immiscible with the mixture resulting from step c and has a lower specific density than the specific density of the mixture resulting from step c; and
   e. stirring the mixture resulting from step d to form a plurality of microspheres each of which encapsulates some of said living tissue cells.

2. A process for encapsulating living tissue cells in a plurality of inorganic microspheres comprising the steps of:
   a. mixing an organosilicon precursor and a hydrolyzing solution which is a highly aqueous acidic solution having a molar concentration of acid in the range of 0.05 to 2.5 to form a gel forming solution wherein said organosilicon precursor is selected from a group consisting of tetraethoxyisilane, tetrabutoxysilane, tetramethoxysilane and tetrapropoxysilane;
   b. mixing living tissue cells and Hanks' Balanced Salt Solution to form a solution containing living tissue cells;

c. mixing the solution containing living tissue cells resulting from step b with the gel forming solution resulting from step a to form a mixture of a specific density;

d. forming droplets of the mixture resulting from step c; and e. putting the droplets resulting from step d into a column of an oil, which is immiscible with the mixture resulting from step c and has a lower specific density than the specific density of the mixture resulting from step c, at the top thereof to form a plurality of microspheres each of which encapsulates some of said living tissue cells.

* * * * *